US 6,589,168 B2

(12) United States Patent  (10) Patent No.: US 6,589,168 B2
Thompson  (45) Date of Patent: Jul. 8, 2003

(54) VIDEO GYNECOLOGICAL EXAMINATION APPARATUS

(76) Inventor: Robert Lee Thompson, 8334 Dogwood La., Rogers, AR (US) 72756

( * ) Notice: Subject to any disclaimer, the term of this patent is extended or adjusted under 35 U.S.C. 154(b) by 0 days.

(21) Appl. No.: 09/930,431

(22) Filed: Aug. 15, 2001

(65) Prior Publication Data

US 2001/0056223 A1 Dec. 27, 2001

Related U.S. Application Data

(63) Continuation of application No. 09/205,883, filed on Dec. 4, 1998, now abandoned, which is a continuation of application No. 08/730,089, filed on Oct. 15, 1996, now Pat. No. 5,846,249.
(60) Provisional application No. 60/011,255, filed on Feb. 7, 1996.

(51) Int. Cl.$^7$ .................................................. A61B 1/32
(52) U.S. Cl. ........................ 600/221; 600/220; 600/223
(58) Field of Search ................................ 600/219–224, 600/201, 119, 235, 109; 248/231.71, 231.41, 354.6, 354.7, 408, 227.4

(56) References Cited

U.S. PATENT DOCUMENTS

| 3,320,948 | A | * | 5/1967 | Martin ........................ 600/205 |
| 3,734,084 | A | | 5/1973 | Ousterhout |
| 3,789,829 | A | * | 2/1974 | Hasson ........................ 600/221 |
| 3,789,835 | A | | 2/1974 | Whitman |
| 3,815,585 | A | * | 6/1974 | Fiore ........................ 600/222 |
| 3,889,661 | A | | 6/1975 | Fiore |
| 4,046,140 | A | | 9/1977 | Born |
| 4,067,323 | A | | 1/1978 | Troutner et al. |
| 4,210,133 | A | | 7/1980 | Castaneda |
| 4,292,965 | A | | 10/1981 | Nash et al. |
| 4,300,541 | A | * | 11/1981 | Burgin ........................ 600/213 |
| 4,538,594 | A | | 9/1985 | Boebel et al. |
| 4,573,452 | A | | 3/1986 | Greenberg |
| 4,585,438 | A | | 4/1986 | Makler |
| 4,619,248 | A | | 10/1986 | Walsh |
| 4,638,792 | A | | 1/1987 | Burgin |
| 4,858,624 | A | | 8/1989 | Shihata |
| 4,905,670 | A | | 3/1990 | Adair |
| 4,979,498 | A | | 12/1990 | Oneda et al. |
| 5,026,368 | A | | 6/1991 | Adair |
| 5,143,054 | A | | 9/1992 | Adair |
| 5,251,613 | A | | 10/1993 | Adair |
| 5,458,595 | A | | 10/1995 | Tadir et al. |
| 5,484,066 | A | | 1/1996 | Luisi |
| 5,499,964 | A | * | 3/1996 | Beck et al. .................. 600/205 |
| 5,505,690 | A | | 4/1996 | Patton et al. |
| 5,509,893 | A | | 4/1996 | Pracas |
| 5,569,254 | A | | 10/1996 | Carlson et al. |
| 5,681,325 | A | | 10/1997 | Hasson |
| 5,810,311 | A | * | 9/1998 | Davison et al. ........ 248/229.26 |
| 5,846,249 | A | | 12/1998 | Thompson |
| RE36,043 | E | | 1/1999 | Knighton |

FOREIGN PATENT DOCUMENTS

| FR | 1126036 | 11/1956 |
| WO | WO 93/20741 | 10/1993 |

* cited by examiner

Primary Examiner—Justine R. Yu
(74) Attorney, Agent, or Firm—Luedeka, Neely & Graham, PC

(57) ABSTRACT

A charge-coupled device camera is removably mounted in a adaptor and the adaptor is removably mounted in the viewing aperture of a speculum. The camera is connected to a display device, such as a video monitor, by a cable. At least one high-intensity light is also mounted in the adaptor with the axis of the light parallel to that of the camera. The light is connected to an adjustable power source by a power supply cord. In one embodiment of the invention, a cervical positioner is provided to allow the physician to align the patient's cervix with the camera's axis for optimal viewing.

10 Claims, 3 Drawing Sheets

VIDEO GYNECOLOGICAL EXAMINATION APPARATUS

This application is a continuation of application Ser. No. 09/205,883, filed Dec. 12, 1998, now abandoned, which is a continuation of U.S. application Ser. No. 08/730,089, filed Oct. 15, 1996, now U.S. Pat. No. 5,846,249, which claims benefit of U.S. provisional application No. 60/011,255, entitled VIDEO GYNECOLOGICAL EXAMINATION APPARATUS, filed Feb. 7, 1996.

FIELD OF THE INVENTION

The present invention is related to an apparatus for conducting gynecological examinations using an electronic image receiving device such as a charge-coupled device.

SUMMARY OF THE INVENTION

A charge-coupled device camera is removably mounted in a adaptor and the adaptor is removably mounted in the viewing aperture of a speculum. The camera is connected to a display device, such as a video monitor, by a cable.

At least one high-intensity light is also mounted in the adaptor with the axis of the light parallel to that of the camera. The light is connected to an adjustable power source by a power supply cord.

In one embodiment of the invention, a cervical positioner is provided to allow the physician to align the patient's cervix with the camera's axis for optimal viewing.

BRIEF DESCRIPTION OF THE DRAWINGS

Two embodiments of the invention will be described, by way of example only, with reference to the accompanying drawings, in which.

DETAILED DESCRIPTION

Figure 1:
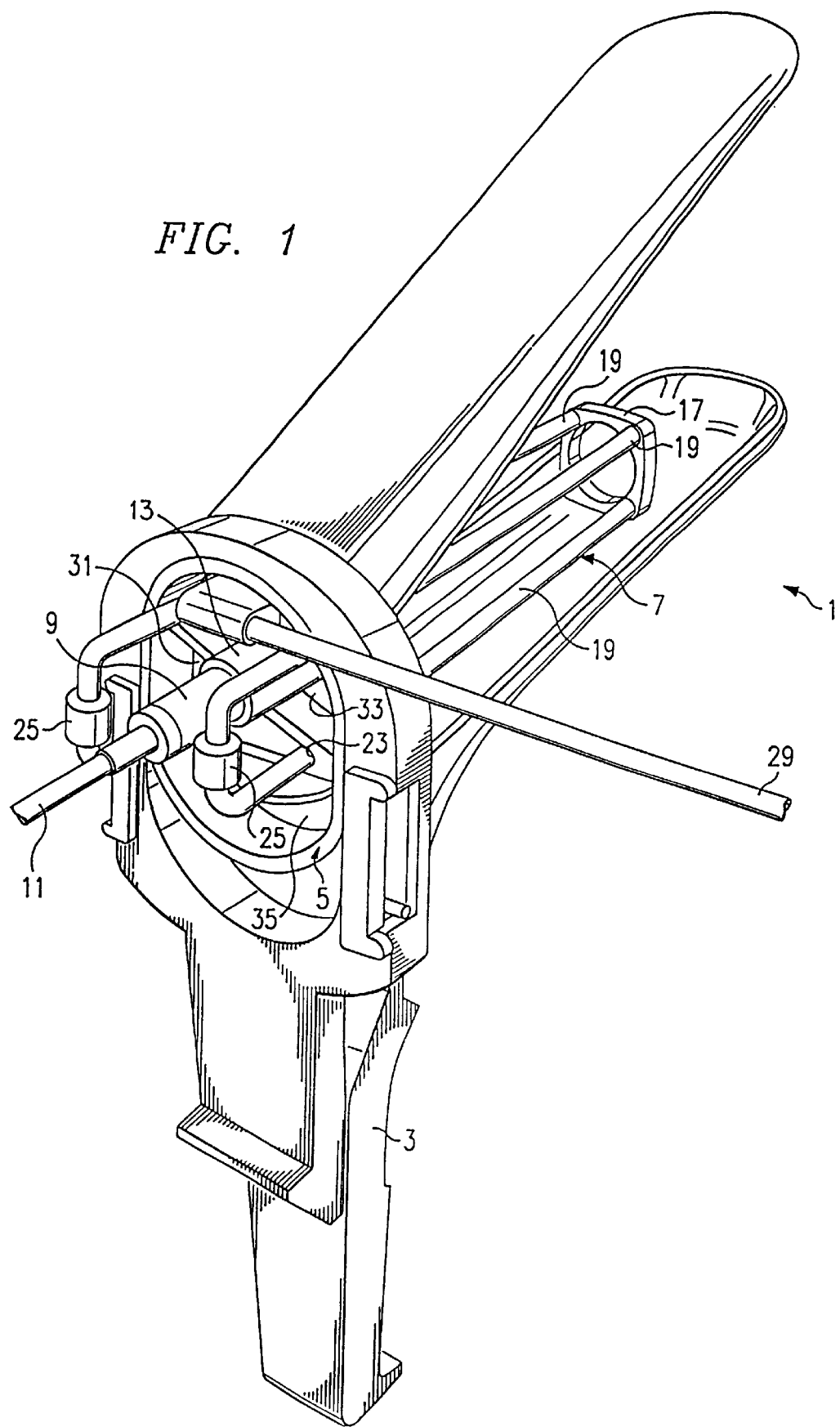
FIG. 1 is a perspective view of a video gynecological examination apparatus embodying the invention.
Figure 2:
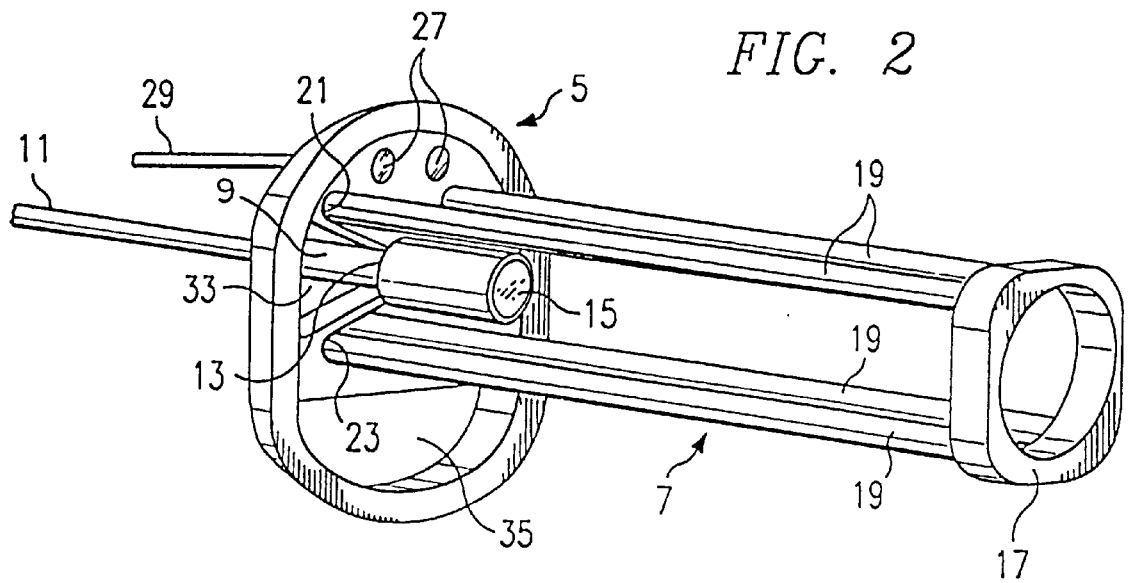
FIG. 2 is an opposing perspective view of the adaptor, camera, and cervical positioner of FIG. 1.

FIGS. 1 and 2 illustrate a video gynecological examination apparatus 1 in accordance with the present invention. The apparatus 1 comprises a conventional speculum 3, an adaptor 5, a movable cervical positioner 7, and a charge-coupled device ("CCD") camera 9. The camera 9 is connected to a video display (not shown) by a camera cable 11.

The adaptor 5 is constructed, for example, of a resilient plastic material, and is "snapped" into place in the speculum 3. In order to accommodate the specula of various manufacturers, a variety of suitably shaped and sized adaptors 5 are provided. The adaptor 5 is supplied in a sterilized condition and is intended to be disposed of after use. Alternately, if desired, the adaptor 5 could be constructed of a suitable material to allow it to be resterilized and reused.

The camera 9 is mounted in an integral camera mount 13. The inside diameter of the aperture in the camera mount 13 is just slightly less than the outside diameter of the camera 9. This allows the camera 9 to be easily inserted and removed.

An optically clear window 15 is sealingly attached to the distal end of the camera mount 13. In use, the position of the portion of the camera 9 that is not within the camera mount 13 is such that it never comes into contact with the patient or any fluids from the patient. As a result, it is not necessary to sterilize the camera 9. This is a significant advantage, as it is not necessary to expose the camera 9 to the heat and/or liquid used in sterilization.

The cervical positioner 7 comprises a plastic cervical ring 17 and four plastic legs 19. To accommodate variations in cervical diameter, the cervical ring 17 is provided in several sizes. The cervical positioner 7 is supplied in a sterilized condition and is intended to be disposed of after use.

The distal end of the legs 19 are press fitted into corresponding orifices in the cervical ring 17. The proximal portions of the legs 19 pass through upper and lower slots 21, 23 in the adaptor 5. The legs 19 are resiliently biased outwardly, resulting in their being pressed against the outer edges of the slots 21, 23. The outer edges of the slots 21, 23 and the surface of the proximal portions of the legs 19 contain teeth (not shown) which cooperate to hold the legs 19 in position relative to the adaptor 5. The orientation of the teeth is such that the legs 19 may be easily pushed distally (from left to right in the drawings) To move the legs proximally (from right to left in the drawings), the legs 19 are moved inwardly to disengage the teeth, then pulled distally.

The proximal ends of the legs 19 on each side of the adaptor are bent toward each other and connected by removable connecting members 25. In use, the legs 19 are moved as required to place the cervical ring 17 around the neck of the patient's cervix (not shown) and to position the patient's cervix in front of the camera 9. If necessary to properly position the cervix, the proximal ends of one or more legs 19 can be removed from the connecting members 25.

Two high-intensity lights 27 provide ample light for conducting an examination. The lights pressed into corresponding apertures in the adaptor 5. A power supply cord 29, connects the lights 27 to a controllable, low-voltage power supply (not shown).

Three apertures 31, 33, 35 are provided in the adaptor 5 to allow access to the patient's cervix when the examination apparatus 1 is in use.

The camera 5 is sensitive to both visible and infrared ("IR") light. To conduct an examination using visible light, the physician places an IR filter (not shown) on the distal end of the camera.

To conduct an examination of a patient's cervix (not shown) the examining physician (not shown) uses the speculum 3 to dilate the patient's vagina (not shown) in the conventional manner. The physician then adjusts the cervical positioner 7 to position the cervical ring 17 about the patient's cervix (not shown) and to position the cervix in front of the camera 9. The physician can then observe the patient's cervix on the display (not shown). If desired, a chemical agent can be applied to the patient's cervix using a conventional swab inserted through one of the apertures 31, 33, 35 in the adaptor 5.

The adaptor 5, cervical positioner 7, and connecting members 25 are provided in a sterilized condition and are intended to be disposed of after use.

Figure 3:
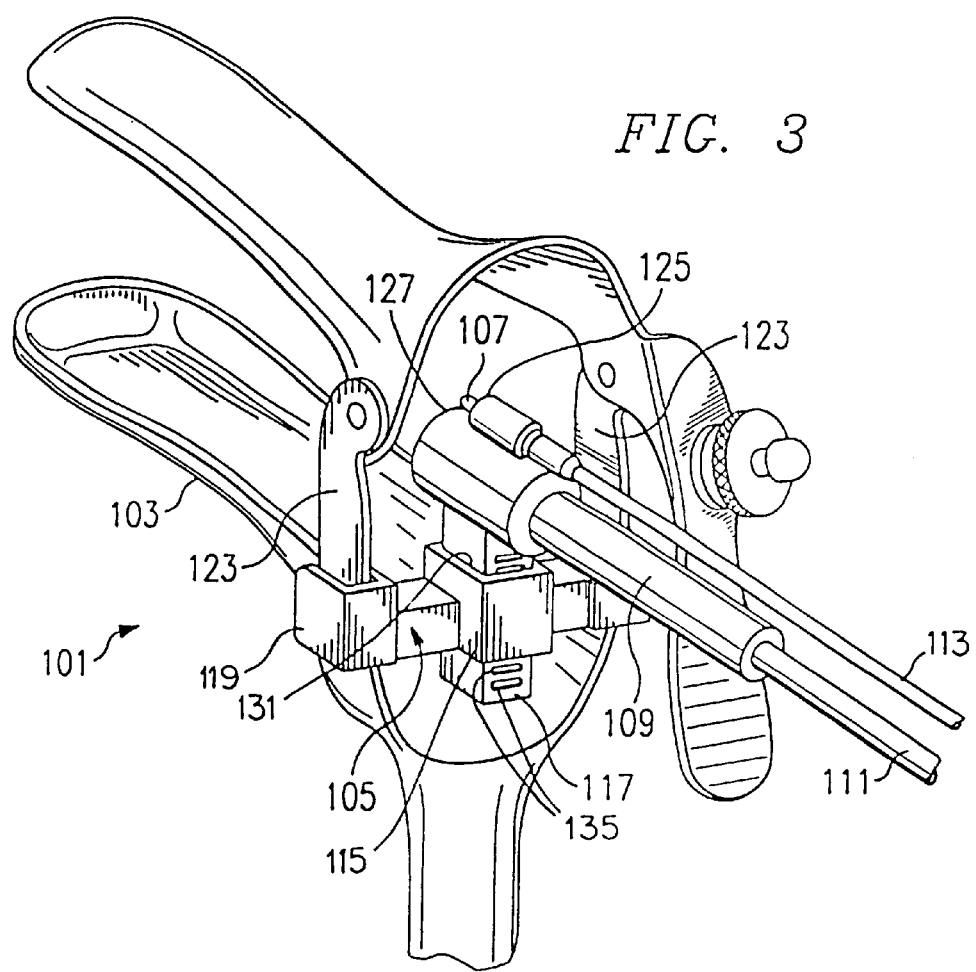
FIG. 3 is a perspective view of a second video gynecological examination apparatus embodying the invention.
Figure 4:
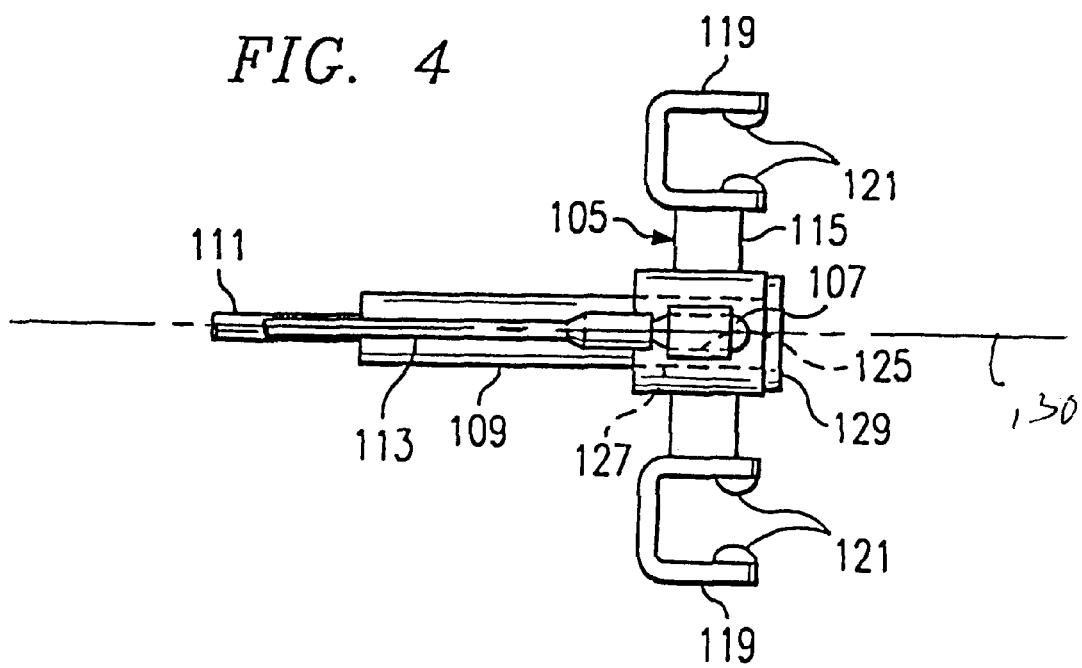
FIG. 4 is a top view of the adaptor and camera of FIG. 3.
Figure 5:
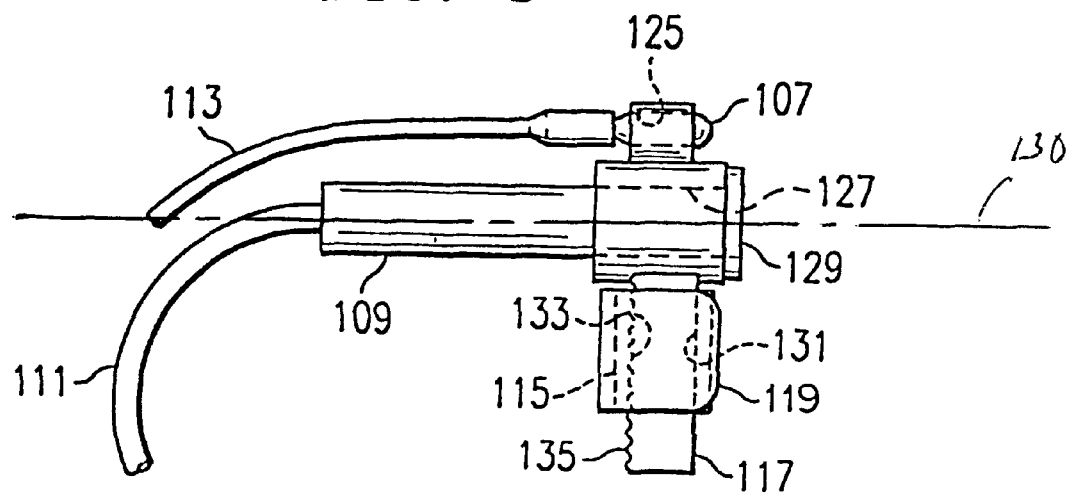
FIG. 5 is a side view of the adaptor and camera of FIG. 3.

FIGS. 3–5 illustrate a second video gynecological apparatus 101 in accordance with the present invention. The apparatus 101 comprises a conventional speculum 103 (only the upper portion of which is shown in FIG. 3), an adaptor 105, a high intensity light 107, and a CCD camera 109. In use, the camera 109 is connected to a video display (not shown) by a camera cable 111, and the light 107 is connected to an adjustable power supply (not shown) by a light cable 113.

As with the apparatus 1 described in connections with FIGS. 1 and 2, the adaptor 105 is constructed of a resilient material, such as plastic, and comprises a horizontal member 115 and a vertical member 117. An integral U-shaped clip 119 is disposed at either end of the horizontal member 115, and each clip 119 includes a pair of inwardly facing projections 121. In use, the adaptor 105 is removably attached to the arms 123 of the speculum 103 by means of the clips 119 on the horizontal member 115.

The upper portion of the vertical member 117 includes a light aperture 125 and a camera aperture 127. An optically clear window 129 is sealingly attached at the distal end of the camera aperture 127. This provides the same advantage discussed in connection with the embodiment of the invention of FIGS. 1 and 2.

The light aperture 125 provides a snug press fit for the high-intensity light 107, and the camera aperture 127 provides a similar fit for the camera 109. As a result, the light 107 and camera 109 can be easily installed in and removed from the adaptor 105.

As with the embodiment of the invention described in connection with FIGS. 1 and 2, the adaptor is constructed of a resilient plastic material, is provided in a sterilized condition, and is intended to be disposed of after use.

The lower portion of he vertical member 117 is slidably disposed in complimentary aperture 131 in the horizontal member 115. The vertical member 117 is retained in position relative to the horizontal member 115 by the engagement of a series of inwardly-extending teeth 133 within the aperture 131 with a corresponding series of indentations 135 in the vertical member 117. As a result, the camera 109 and light 107 are vertically adjustable within the viewing aperture of the speculum 103. This allows the light 107 and axis 130 of camera 109 to be positioned for optimal viewing of the area of interest.

I claim:

1. Gynecological examination apparatus, comprising:
   a speculum having a first blade, a second blade, and a pair of spaced apart arms adjustably connecting the first blade to the second blade so that the first blade is movable relative to the second blade;
   an elongate first adaptor member having opposite ends and extending between the pair of arms of the speculum, each end of the first adaptor member being configured to frictionally engage one of the arms of the speculum to enable the first adaptor member to be frictionally mountable to the arms of the speculum, the first adaptor member further including an intermediate portion thereof defining an aperture; and
   a second adaptor member having a first section configured for being received within the aperture of the intermediate portion of the first adaptor, and a second section located adjacent the first section of the second adaptor and configured for receiving a camera,
   wherein the aperture of the intermediate portion of the first adaptor member includes a series of inwardly extending teeth, and the first section of the second adaptor member includes a corresponding series of indentations, wherein the teeth and the indentations cooperate to enable the position of the second adaptor member to be adjusted relative to the first adaptor member.

2. The apparatus of claim 1, wherein each end of the first adaptor member composes a U-shaped clip having a pair of inwardly facing projections.

3. The apparatus of claim 1, wherein the second section of the second adaptor member includes an aperture sized to provide a substantially snug press fit for a camera received therein.

4. The apparatus of claim 1, wherein the second section of the second adaptor member is further configured for receiving a light.

5. The apparatus of claim 4, wherein the second section of the second adaptor member includes a first aperture sized to provide a substantially snug press fit for a camera received therein and a second aperture sized to provide a substantially snug press fit for a light received therein.

6. An adaptor for positioning a camera relative to a gynecological examination speculum of the type having a first blade, a second blade, and a pair of spaced apart arms adjustably connecting the first blade to the second blade so that the first blade is movable relative to the second blade, the adaptor comprising:
   an elongate first adaptor member having opposite ends and extending between the pair of arms of the speculum, each end of the first adaptor member being configured to be frictionally engagable with one of the arms of the speculum to enable the first adaptor member to be frictionally mountable to the arms of the speculum, the first adaptor member further including an intermediate portion thereof defining an aperture; and
   a second adaptor member having a first section configured for being received within the aperture of the intermediate portion of the first adaptor, and a second section located adjacent the first section of the second adaptor member and configured for receiving a camera,
   wherein the aperture of the intermediate portion of the first adaptor member includes a series of inwardly extending teeth, and the first section of the second adaptor member includes a corresponding series of indentations, wherein the teeth and the indentations cooperate to enable the position of the second adaptor member to be adjusted relative to the first adaptor member.

7. The apparatus of claim 6, wherein each end of the first adaptor member comprises a U-shaped clip having a pair of inwardly facing projections.

8. The apparatus of claim 6, wherein the second section of the second adaptor member includes an aperture sized to provide a substantially snug press fit for a camera received therein.

9. The apparatus of claim 6, wherein the second section of the second adaptor member is further configured for receiving a light.

10. The apparatus of claim 9, wherein the second section of the second adaptor member includes a first aperture sized to provide a substantially snug press fit for a camera received therein and a second aperture sized to provide a substantially snug press fit for a light received therein.

* * * * *